US010463313B2

(12) United States Patent
Koutsouleris et al.

(10) Patent No.: US 10,463,313 B2
(45) Date of Patent: Nov. 5, 2019

(54) ADAPTIVE PATTERN RECOGNITION FOR PSYCHOSIS RISK MODELLING

(71) Applicants: Nikolaos Koutsouleris, Munich (DE); Eva Meisenzahl-Lechner, Munich (DE)

(72) Inventors: Nikolaos Koutsouleris, Munich (DE); Eva Meisenzahl-Lechner, Munich (DE)

(*) Notice: Subject to any disclaimer, the term of this patent is extended or adjusted under 35 U.S.C. 154(b) by 823 days.

(21) Appl. No.: 14/910,588

(22) PCT Filed: Aug. 5, 2014

(86) PCT No.: PCT/EP2014/002154
§ 371 (c)(1),
(2) Date: Feb. 5, 2016

(87) PCT Pub. No.: WO2015/018517
PCT Pub. Date: Feb. 12, 2015

(65) Prior Publication Data
US 2016/0192889 A1 Jul. 7, 2016

(30) Foreign Application Priority Data

Aug. 5, 2013 (EP) .................................... 13003908

(51) Int. Cl.
*A61B 5/00* (2006.01)
*A61B 5/055* (2006.01)
(Continued)

(52) U.S. Cl.
CPC ............ *A61B 5/7275* (2013.01); *A61B 5/055* (2013.01); *A61B 5/4088* (2013.01); *G16H 50/30* (2018.01); *G16H 50/70* (2018.01)

(58) Field of Classification Search
None
See application file for complete search history.

(56) References Cited

U.S. PATENT DOCUMENTS 9,195,949 B2 * 11/2015 Kasabov ................. G06F 19/24
9,582,647 B2 * 2/2017 Kenedy ................... G16H 50/30
(Continued)

OTHER PUBLICATIONS

Ye et al., Heterogeneous Data Fusion for Alzheimer's Disease Study, ACM, 2008, pp. 1025-1033 (Year: 2008).*

*Primary Examiner* — Alan Chen
(74) *Attorney, Agent, or Firm* — Stein IP, LLC

(57) ABSTRACT

The present invention relates to a method and a system for an adaptive pattern recognition for psychosis risk modeling with at least the following steps and features: automatically generating a first risk quantification or classification system on the basis of brain images and data mining; automatically generating a second risk quantification or classification system on the basis of genomic and/or metabolomic information and data mining and further processing the first and second risk quantification or classification systems by data mining computing so as to create a meta-level risk quantification data to automatically quantify psychosis risk at the single-subject level. Preferably the first and/or second risk quantification or classification system(s) extract specific surrogate markers by multi-modal data acquisition and/or the surrogate markers are categorized and/or quantified by a multi-axial scoring system. Data can be controlled and outliers can be detected and eliminated preferably by determining cut-off thresholds. More preferably an outlier detection method transfers the brain image into a calibrated image, a segmented image and/or a registered image. Uni-modal data can be further generated and optionally optimized on the basis of the data acquired and one or more similarity and/or dissimilarity between the multi-modal data and the uni-modal data can be quantified.

18 Claims, 6 Drawing Sheets

(51) Int. Cl.
*G16H 50/30* (2018.01)
*G16H 50/70* (2018.01)

(56) References Cited

U.S. PATENT DOCUMENTS

| | | | |
|---|---|---|---|
| 2006/0099624 A1* | 5/2006 | Wang | G01N 33/6896 435/6.12 |
| 2011/0119212 A1* | 5/2011 | De Bruin | A61B 5/00 706/12 |
| 2013/0039552 A1* | 2/2013 | Becker | G06F 19/321 382/128 |
| 2013/0275350 A1* | 10/2013 | Schaffer | G06N 99/005 706/12 |

* cited by examiner

ADAPTIVE PATTERN RECOGNITION FOR PSYCHOSIS RISK MODELLING

CROSS-REFERENCE TO RELATED APPLICATIONS

This application is a national stage of International Application No. PCT/EP2014/002154, filed Aug. 5, 2014, which claims the benefit of priority to European Application No. 13003908.4, filed Aug. 5, 2013, in the European Patent Office, the disclosures of which are incorporated herein by reference.

BACKGROUND OF THE INVENTION

The present invention relates to the field of psychiatric risk modelling or psychosis risk quantification, particularly to the field of adaptive pattern recognition therefor. The invention relates to a respective method, system, data carrier with a computer program being able to carry out the method, a telemedicine system and other related entities.

PRIOR ART

Affective and non-affective psychoses have a major negative impact on human society. They account for 6.3% of the global burden of disease and cost € 207 billion per year in Europe alone, making them the most expensive brain-related disorders and even more expensive than cardiovascular diseases (€ 169 billion). This immense socio-economic burden is largely caused by two core features of affective and non-affective psychotic illnesses, their onset in adolescence and early adulthood and their long-term disabling courses and outcomes. Both factors lead to enduring social and vocational exclusion and contribute to 8-20 times higher suicide rates in affected patients. The early recognition of psychoses is characterised by a limited number of specialised mental health services in Europe and around the world. These services employ different clinical early detection inventories to recruit at-risk mental states (ARMS) persons mainly within research-oriented institutional contexts. However, this approach has so far not lead to broadly accessible tools for psychoses risk assessment that operate accurately and reliably at the single-subject level.

Up to now, the early recognition of psychosis is restricted in three ways: (i) it is structurally confined to a few specialised early detection services, (ii) it is clinically bound to the elaborate evaluation of subtle prodromal symptoms indicative of an elevated disease vulnerability, and (iii) it is methodologically limited by the reductionist group-level modelling of the disease's complex, highly interdependent features. Despite these limitations, the currently used clinical early recognition inventories achieved the first step for personalised psychoses prevention: they allowed for the identification of individuals at risk for mental illness and chronic disability. Based on this risk enrichment procedures and univariate statistical methods previous studies described neuroanatomical, neurofunctional and neurocognitive alterations in relatively small ARMS samples, which may constitute the neurobiological underpinnings of these at-risk and prodromal states of psychoses.

However, the designs and analysis strategies employed in these studies prohibit the use of the respective findings for single-subject prognostic purposes.

Early recognition research has revealed that patterns of subtle prodromal symptoms allow persons with clinical at-risk mental states (ARMS) for psychoses to be reliably identified. These clinically defined ARMS individuals have a hundred-fold higher risk for developing these devastating mental illnesses than the general population. However, relying solely on these symptoms leads to a correct 24-month prediction of psychoses in only ~30% of these persons.

ARMS individuals are also at risk of enduring social and occupational impairment, irrespective of whether they ultimately transition to psychosis. In this regard, converging evidence is provided that the probability of adverse clinical and functional outcomes is determined by the presence of non-remitting sub-threshold psychoses, substance abuse and comorbid axis-I and axis-II diagnoses. These concomitant psychiatric conditions include in particular mood, anxiety and personality disorders in the large majority of at-risk persons. Thus, the prevention of functional disability due to non-psychotic conditions in these non-converted, but still impaired at-risk individuals requires reliable prognostic tools that identify these diverse risk factors at the single-subject level. As suggested by the present invention, these tools will result from integrated research activities that (i) collate multi-modal databases covering multiple risk axes of psychosis development and (ii) analyse these databases with novel machine learning systems capable of decomposing the phenotypes currently subsumed under the at-risk concept into a plurality of risk-conferring factors. Such prognostic tools will enable the implementation and validation of fine-grained, personalised therapies for adverse outcome prevention. Hence, they will facilitate a substantial and sustainable reduction of the mental health-related socioeconomic burden worldwide.

An equally important target of early recognition is the prediction of disease chronification after the initial phase of psychotic illnesses. In particular, the association between longer duration of untreated psychoses and poorer disease outcomes is a well-replicated finding, highlighting the importance of reducing the time between the onset of symptoms and the commencement of therapy. Indeed, previous studies have demonstrated significantly lower levels of psychotic symptoms, higher rates of paid employment and in consequence significant cost reductions through early intervention in the recent-onset stage of psychoses (ROP). As outlined in our proposal, augmenting this approach with aspect prognostic tools that pinpoint ROP patients with chronic and disabling disease courses will considerably improve personalised care, outcomes and cost effectiveness of early intervention. This progress will foster the implementation of early recognition services across healthcare systems.

Thus, in summary there is a pressing need for an individualised and aspect prediction of critical clinical and functional outcomes across all ARMS and stages of psychoses, ranging from initial depressive syndromes to the early and established phases of these diseases.

SUMMARY OF THE PRESENT INVENTION

It is a preferred object to provide an improved method, system, computer implemented program and data carrier with such program, a telemedicine system and other related entities.

The afore-mentioned object is attained by the subject-matter according to the present invention. The present invention and particularly preferred aspects and embodiments thereof are defined in the claims.

The present invention is applied without a patient being personally involved in the pattern recognition-based psychosis risk quantification or classification process or any other aspect according to the present invention as will be further highlighted in the following.

The present invention particularly relates to a method for an adaptive pattern or classification recognition for psychosis or psychological or psychiatric risk determination or modelling. A first fully automated risk classification or quantification system (regression-based or classification-based risk modelling) is provided on the basis of brain images and data mining. Furthermore, a second fully automated risk quantification or classification system is provided on the basis of genomic and/or metabolomic information and data mining. The first and second risk quantification or classifisystems are computed by data mining so as to create meta-level risk quantification data and a respectively trained meta-level system to automatically quantify psychosis risk at the single-subject level.

According to a further preferred aspect specific surrogate markers are extracted by multi-modal data acquisition, particularly for the first and/or second risk quantification system(s).

More preferably, the surrogate markers are categorized or quantified by a multi-axial scoring system that may consist of the following processing computation steps:

Pre-processing: For the first risk quantification system a pre-processing method transfers the brain image into a calibrated image, by e.g. segmenting the image into different tissue components and registering these components to a stereotactic template image. Further preferred aspect is at least one post hoc scanner calibration method which is employed for the brain or other kind of images and which is adapted to minimize scanner-induced variance and/or harmonize new scanners with already used scanners.

First-pass outlier detection: Pre-processed images are controlled for their outlierness. The detection and elimination of outliers is preferably performed for the first and/or second risk quantification system(s) by one-class SVM, Support Vector Data Description (SVDD) and/or k-Nearest Neighbour Data Description (kNNDD) methods.

Uni-modal risk quantification systems: According to a further preferred aspect of the present invention, uni-modal risk quantification systems are optimized on the basis of single data channels (e.g. structural MRI) The optimization process is performed stepwise: First, one or more feature selection methods, such as margin-based feature selection methods, are used to rank features, such as voxels, according to their relevance for the predicting risk-conferring end-points (=markers). Second, the first-step feature selection methods pass the uni-modal data to a further processing step, consisting of dimensionality reduction methods such as a principal component analysis. This step is used to obtain compact sets of discriminative and/or predictive features by further attenuating noisy or irrelevant information. Third, the sets of discriminative and/or predictive data are further preferably forwarded to uni-modal machine learning methods (e.g. SVM, RVM) to detect separating hyper planes (OSH) for risk-related classification, and to preferably provide decision scores for each classified subject according to the respective geometric distance to the OSH. Fourth, uni-modal machine learning methods are wrapped into model validation techniques such as bootstrapping or k-fold cross validation in order to create uni-modal committee-based risk quantification systems.

Multi-modal data integration: the fusion of predictive information across different data domains (e.g. structural MRI, Diffusion-Tensor-Imaging, resting-state fMRI) is preferably carried out by means of committee-based optimization processes which combine the thos uni-modal base learners across domains that conjointly improve risk quantification. The preferred aspect of this data fusion method is that the multi-modal committee-based risk quantifier is more robust to data loss or failure of the underlying uni-modal risk quantifiers.

Second-pass outlier detection: A further preferred aspect of the present invention is to control the subject images for outliers across uni-modal data domains. This step is preferably carried out using the one-class machine learning methods specified in the first-pass outlier detection step.

Multi-axial risk quantification: According to a further preferred aspect of the present invention a multi-axial scoring system is provided which is adapted to perform a second-level machine learning optimization, preferably one or more advanced ensemble learning method(s), comprising generalized ensemble methods, stacked generalization, heterogeneous ensemble methods, and preferably one or more method(s) for diverse base learner selection and ensemble generation. These methods comprise a learning of one or more risk-related prediction rules, which together capture target outcome risk (e.g. transition to psychosis) in a more generalizable way than the immediate modelling of these risk targets in a single-level machine learning process This aspect embraces the integration of a plurality of risk-conferring surrogate markers into a multi-axial risk profile. Meta-classifiers are preferably trained using the multi-axial profiler data for distinguishing between individuals with a subsequent transition or non-transition to psychosis.

Final risk classification: According to a further preferred aspect of the present invention a psychosis risk of an individual can be examined or determined by applying a pattern, classification and/or model obtained by one of the preceding aspects and/or embodiments. These aspects and/or embodiments relate to the establishment of an automated pattern or classification recognition method or system. Once the data mining and machine learning processes have generated such a system it can be applied for determining risks or classifying psychoses or psychotic or psychiatric challenges.

Neuromonitoring: Moreover any psychosis progression or regression and be monitored or determined by repeating the before described aspects and/or embodiments. Individuals will therefor undergo multiple examinations preferably at pre-set intervals.

Telemedicine platform for risk quantification: According to a further preferred aspect a network-based platform is established, preferably on the basis of an encrypted telemedicine platform.

Further preferably adaptive Multi-Agent Systems (MAS) are used to personalise the performance of telemedicine platform or applications to the risk profile of the individual subject (e.g. help sucker).

According to a further aspect of the present invention diagnostic streams are created and personalized by one or more of the following steps: initialising agents for a given diagnostic, comprising agents for data acquisition, processing and/or result reporting; forming modality-specific diagnostic layers that have a built-in logic for organizing agents into information processing streams, such as acquisition, calibration, segmentation, normalization and/or outcome prediction of structural MRI data, preferably monitored by a data quality control agent; adapting the agent selection process by integrating process variables such as prognostic outcome (post-test probability), a multi-axial risk-conferring profile of the help-seeker; and/or diagnostic constraints of given clinical situations (e.g. costs, invasiveness, duration and quality of examinations).

The present invention also covers a computer-related product carrying out the method according to any one of the preceding aspects or embodiments. A data carrier with such a computer related product is also covered by the present invention.

Moreover, the invention preferably also refers to any system or hardware entity that realizes any of the above or below described or claimed method aspects or embodiments. In particular, the present invention preferably also relates to a system for an adaptive pattern for psychosis risk modelling with at least the following features: a first fully automated risk quantification system on the basis of brain images or other images and data mining; a second fully automated risk quantification system on the basis of genomic and/or metabolomic information by means of data mining and a meta-level risk quantification system adapted to further process the first and second risk quantification systems by data mining computing so as to automatically quantify psychosis risk at the single-subject level in new test subjects.

The present invention also concerns a system for prospectively quantifying the risk of an individual person (using pattern regression or classification algorithms) for repeatedly monitoring the development of psychosis-related disease signatures of the individual over time.

One embodiment of making the invention accessible to a larger number of users is to establish a correspondingly assembled platform. For data protection reasons this platform can contain encrypted data, particularly of an individual, which can be decrypted by one or more authorized user devices, such as computers, terminals, handheld computers etc.

These present invention will preferably provide accurate and adaptive pattern recognition for psychosis risk quantification. The early recognition methods and tools enable to determine and to treat such psychoses at a very or at least earlier stage than the current state-of-the-art with preferably increased accuracy, reliability and generalizability across centres, healthcare systems and patient populations.

The present invention provides a method, a system and further related entities that enable and expand the personalised prediction of mental health-related outcomes or psychoses, particularly in an automated manner.

According to one aspect of the present invention reliable and broadly accessible prognostic tools will significantly alleviate this disease burden by enabling individualised risk prediction, thus paving the way to the targeted prevention of psychoses. Therefore, first brain imaging and preferably complementary data (such as genetic or metabolic information) is used to optimise candidate biomarkers for the prediction and staging of psychoses and to generate a prognostic system that generalises well across any region, such as the European, United State's and/or Asian mental health services. Further, new multi-modal risk quantification tools are developed and validated to reliably predict mental health-related disability in young help-seeking persons. The fusion of these novel prognostic tools produce prognostic services that accurately identify help-seekers at the highest risk of psychotic illnesses, poor functioning and suicide-related mortality.

Such knowledge is preferably exploited through internet-based telemedicine applications. Target groups include caregivers of varying specialisation level, the pharmaceutical industry as well as research institutions developing novel surrogate markers for neuropsychiatric disorders. By enabling and disseminating aspect risk quantification at the single-subject level, these products will provide firm diagnostic grounds for the commencement of preventive interventions, improving outcomes and reducing costs.

Imaging biomarkers are particularly suited for early detection and are also provided according to a preferred aspect of the present invention. Replicated findings have provided evidence that structural and functional neuroimaging acts as the central pace maker for the development of such surrogate markers. Neuroimaging has allowed for the quantification of psychoses-related risk along two critical axes: risk of disease transition and risk of functional disability.

The invention further supports the utility of combining structural MRI with advanced machine learning methods for predicting psychoses across centres and scanners. These observations are in line with recent multi-site studies that achieved high cross-validated accuracies in the diagnostic classification of Alzheimer's disease and major depression despite heterogeneous scanner hardware.

Neurocognitive and clinical prediction models have confirmed the neuroimaging-based prediction of psychoses. In particular, the inventors observed predictive neurocognitive signatures of emerging psychosis, detected using cross-validated support vector classification.

These observations show that the information needed for a reliable single-subject prediction of psychoses is not solely confined to neuroimaging data but is rather distributed across different data dimensions and modalities. Possibly, these distributed information profiles constitute multi-modal signatures of psychoses-related risk. Thus, multi-modal prognostic surrogate markers combining neuroimaging data with complimentary sources of information, like behavioural, genetic and metabolic data, provide even higher levels of diagnostic certainty. This is backed by recent studies.

In this regard, building on results in the uni-modal machine learning analysis of sMRI and neurocognitive data, the candidate biomarkers for psychoses prediction can be (i) optimised by integrating them into multi-modal prognostic models, (ii) improved by using advanced ensemble learning and machine learning methods capable of dealing with censored data, and (iii) validated and disseminated across larger at-risk populations and healthcare settings.

Further aspects and advantages of the present invention are described in the scientific paper "Detecting the Psychosis Prodrome Across High-risk Populations Using Neuroanatomical Biomarkers" published on Jun. 9, 2014 in the Schizophrenia Bulletin by Oxford University Press which is herewith incorporated by reference.

DESCRIPTION OF THE FIGURES AND TABLES

Tab. 1 lists one embodiment of group-specific inclusion and exclusion criteria as well as general study exclusion criteria defined for participant recruitment across all study centres; and Tab. 2 shows participants for these four study groups and how they are recruited at 6 European centres;

Tab. 3 corresponds to a preferred embodiment with preferred different components of telemedicine methods and devices in accordance with the present invention;

Tab. 4 shows results of Kaplan-Meier survival analysis for neuroanatomical low-, intermediate- and high-risk groups;

FIG. 1 shows a proof-of-principle study for the generalisation of MRI-based prediction systems beyond a single centre with samples of the prediction of transition (ARMS-T) vs. non-transition (ARMS-NT) to psychoses in 66 ARMS individuals on the basis of MRI data pooled;

FIG. 2 exemplifies the diversity of study access pathways and personnel involved in case management as well as in the different baseline and follow-up examination modules;

Figure 5:
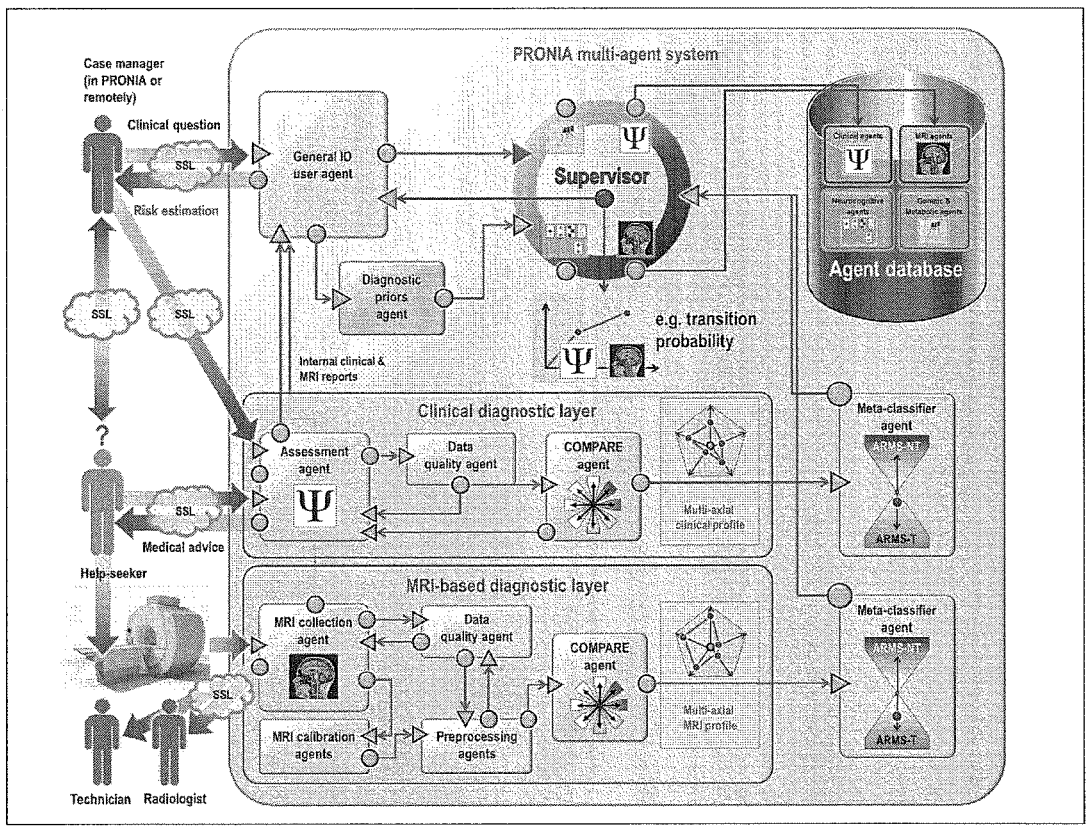
Figure 6:
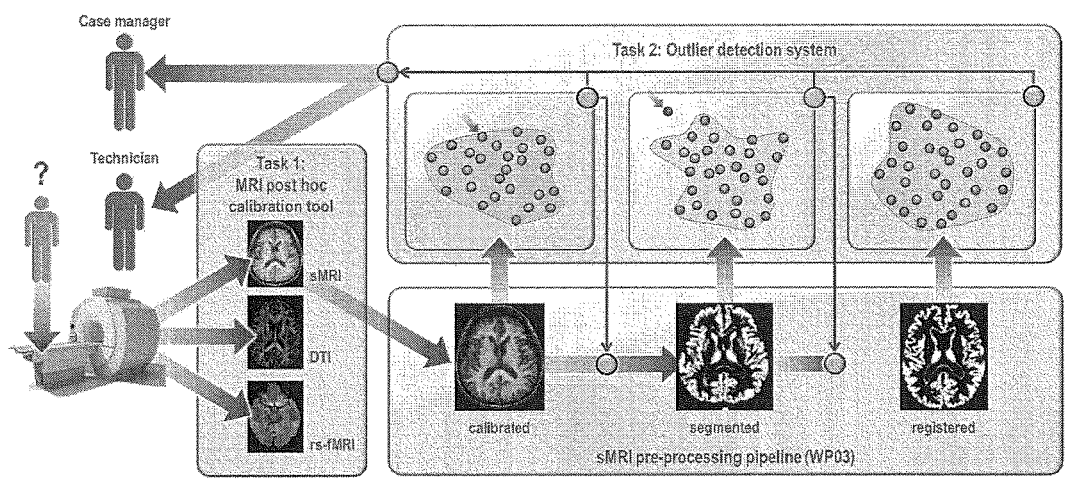
Figure 7:
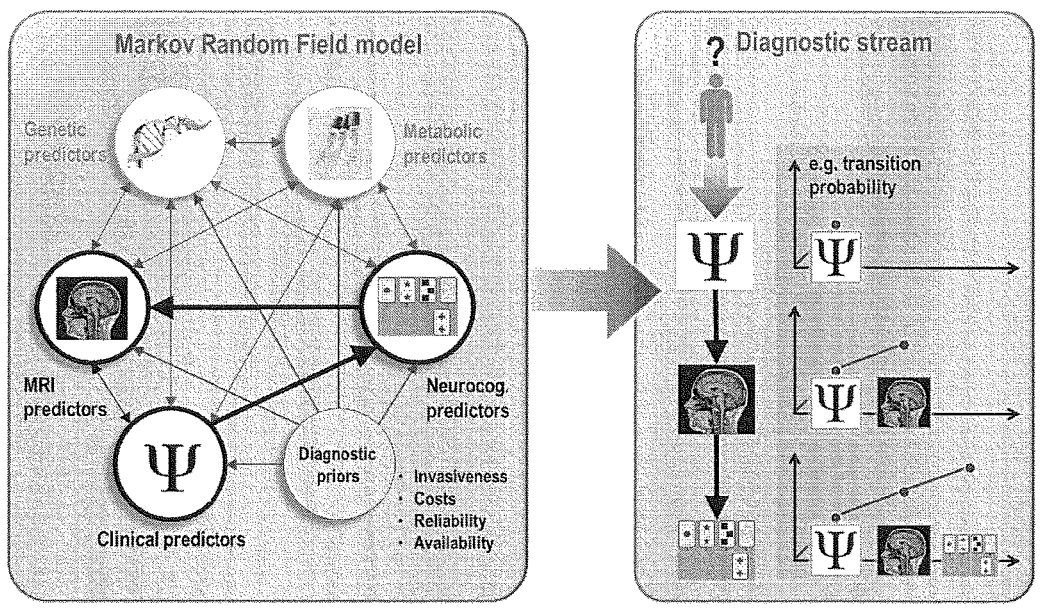
Figure 9:
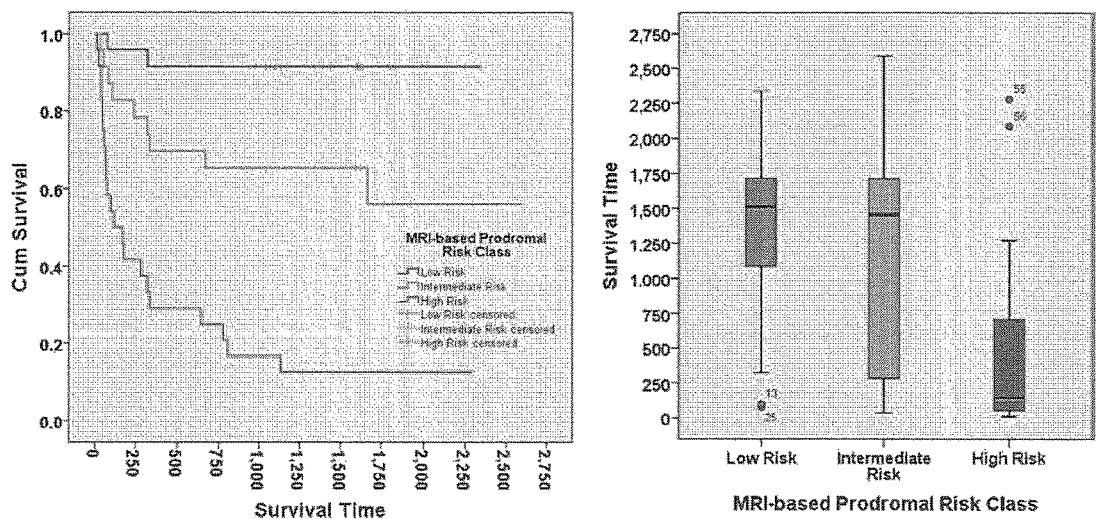
Figure 8:
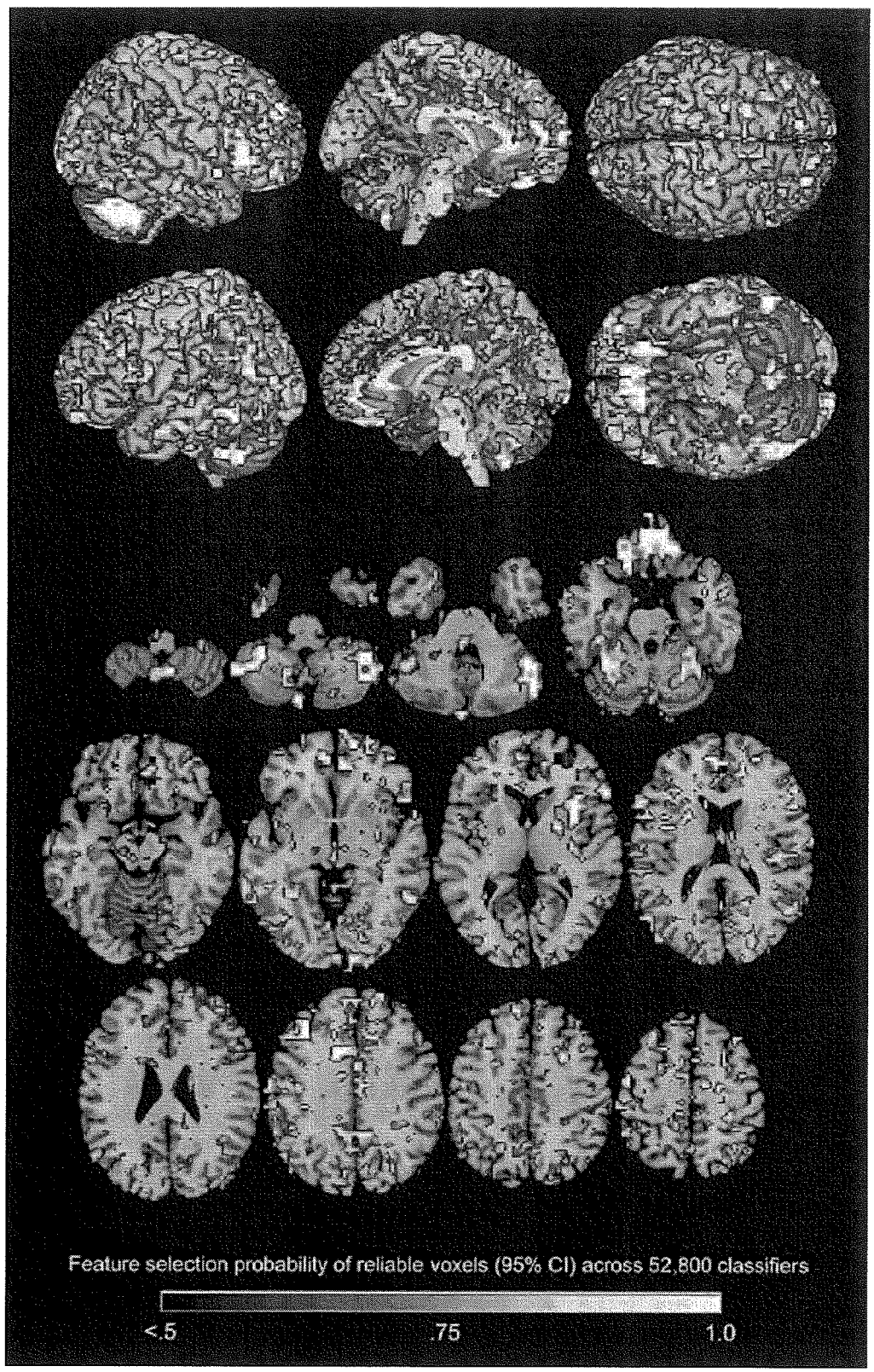

FIG. 5 exemplifies steps of a possible diagnostic stream within the present invention's tentative multi-agent system;

FIG. 6 exemplifies a preferred embodiment of described quality control modules on the MRI pre-processing pipeline in accordance with the present invention;

FIG. 7 shows a preferred diagnostic stream generated by the Markov Random Field (MRF) approach;

FIG. 8 exemplifies a voxel probability map of reliable contributions to the ARMS-NT vs ARMS-T decision boundary; and FIG. 9 shows on the left a comparison of Kaplan-Meier survival curves in ARMS individuals with a low, intermediate, and high neuroanatomical risk level.

DESCRIPTION OF THE PREFERRED EMBODIMENTS

Non-limiting and exemplifying examples and/or aspects of the present invention are described below.

The applicants' existing pattern recognition tool NeuroMiner was used to implement a fully automated machine learning pipeline, which (1) constructed sets of predictive neuroanatomical features from high-dimensional GM maps, and (2) learned decision rules from these features to predict psychosis at the single subject level. To strictly separate the training process from the evaluation of the predictor's generalization capacity, the pipeline was completely embedded into a repeated, double cross-validation framework (rdCV). rdCV computes an unbiased estimate of the method's expected diagnostic accuracy on new cases, rather than merely fitting the current study population. Furthermore, rdCV produces predictor ensembles that optimally separate single individuals from different groups, while avoiding overfitting to the peculiarities of the training data. More specifically, the following analysis steps were wrapped into a Leave-One-Per-Group-Out cross-validation cycle at the outer (CV2) and the inner (CV1) cycles of rdCV: each training sample's GM tissue maps were initially corrected for center effects using partial correlation analysis and scaled voxel-wise to the range [0,1]. These maps entered a multivariate local linear learning algorithm that weighted voxels according to the geometric distance ("margin") they conjointly induced between the ARMS-NT and ARMS-T classes. The algorithm's parameters were a priori set to $\sigma=2$ and $\lambda=0.5$ to extract sparse, non-redundant voxel sets from the data. To further reduce feature dimensionality, subsets of correlated voxels within the extracted patterns were projected to uncorrelated principal components (PC) using Robust Principal Component Analysis. These PC features entered a linear v-SVM algorithm (LIBSVM, (http://www-.csie.ntu.edu.tw/~cjlin/libsvm/) that determined the optimal between-group boundary by maximizing the margin between the neuro-anatomically most similar subjects of opposite groups (the "support vectors"). Optimal PC number and v parameters were determined for each training sample within the inner rdCV cycle. Finally, unseen CV1 and CV2 test subjects were processed by successively applying all training parameters to the test data: adjustment for center effects (partial correlations), voxel-wise scaling and weighting, dimensionality reduction, and linear kernel projection. Within kernel space, the SVM classifier determined a test subject's geometric position relative to the learned decision boundary, resulting in a decision value and a group membership prediction. This analysis sequence was repeated for each CV1 training partition in a given CV2 training fold, thus generating an ensemble classifier which computed a CV2 test subject's group membership by averaging the decision scores of its SVM base learners (Supplementary Methods). Finally, for each subject, ensemble decisions were aggregated across those partitions, in which this subject had not been involved in the training process. Majority voting was used to determine the test subject's class probability, and thus its final out-of-training (OOT) group membership. Moreover, the trained prediction system to the MRI data of the 7 ARMS-NT individuals was applied, who were initially removed from the database. The predictive signature was visualized by computing the average voxel probability map across the entire rdCV structure as shown in FIG. 8. Moreover, a parcellation analysis (Tab. 4) measured the distribution of reliably predictive voxels across the 116 brain regions of the AAL template (Automated Anatomical Labeling). Two additional analyses were carried out using the same parameter setup as described above (Supplementary Results Further aspects and advantages of the present invention are described in the scientific paper "Detecting the Psychosis Prodrome Across High-risk Populations Using Neuroanatomical Biomarkers" published on Jun. 9, 2014 in the Schizophrenia Bulletin by Oxford University Press which is herewith incorporated by reference). In Supplementary Analysis 1 of this scientific paper the strength was quantified of between-center effects comprising MRI and population-related differences, as well as the capacity of the correction method to mitigate these effects. Supplementary Analysis 2 in the afore-mentioned scientific paper measured how an ARMS-T sample size reduction in two-, four-, and six-out experiments affected OOT predictions and generalization to the independent test sample, extended by the left-out subjects. Finally, a Kaplan-Meier survival analysis was performed in the entire ARMS population to assess the time dependency of transition with respect to neuroanatomical risk as defined by the subjects' decision scores. Therefore, the cohort's decision values were split into 33%-quantiles that assigned subjects to "low," "intermediate," and "high-risk" levels. Median survival times, transition rates, and recruitment center compositions were compared between risk levels using median and chi-square tests. Pairwise differences between survival functions were evaluated using log-rank tests.

The integration of neuroimaging with novel multivariate pattern recognition methods facilitates individualised diagnosis across diverse neuropsychiatric diseases, including schizophrenia and ROP. Beyond the psychoses field, these MRI-based machine learning methods also succeeded in predicting subsequent neurodegenerative disorders in prodromal individuals, thus emphasizing their potential for neurodiagnostic illness prediction prior to disease onset. In line with these observations, MRI-based prediction of psychoses is feasible in two independent at-risk cohorts, yielding classification accuracies of ~85%.

The integration of imaging biomarkers into clinical risk assessment protocols raises diagnostic certainty by 35%-40%, thus attaining levels required for targeted preventive treatment. Furthermore, a single-subject MRI-based staging of psychoses paves the way for an aspect stratification of therapeutic interventions.

Finally, longitudinal neuroimaging studies provided evidence for progressive brain alterations occurring across the prodromal and recent-onset stages of psychoses.

These findings support that dynamic brain changes evolve along neuroanatomical disease trajectories, which can be predicted at the single-subject level by means of multivariate pattern regression.

Neurodiagnostic tools to monitor these trajectories allow (i) the MRI-based prognosis of clinical and functional outcome in at-risk individuals to be refined, and (ii) surrogate markers of clinical deterioration and remission to be detected, thus enabling early determination in the course of the illness.

Figure 1:
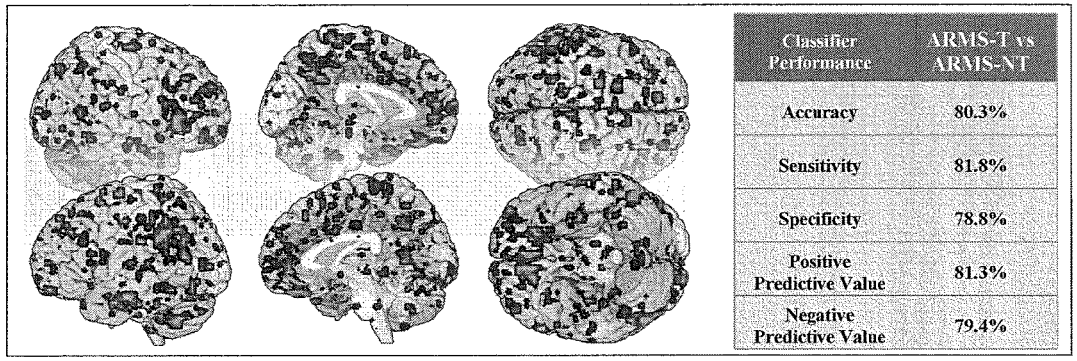

FIG. 1 shows the prediction of transition (ARMS-T) vs. non-transition (ARMS-NT) to psychoses in 66 ARMS individuals on the basis of MRI data pooled. Data were acquired with two different MRI scanners and protocols. Left: Brain regions involved in disease prediction. Right: Classifier performance in out-of-training individuals. FIG. 1 thus constitutes a proof-of-principle study.

The candidate biomarkers allow operating across larger at-risk cohorts. Neuroimaging has already facilitated the diagnostic classification of neurodegenerative diseases across scanners and patient cohorts.

In this regard, FIG. 1 shows that the MRI-based prediction of psychoses is also feasible across early recognition centres. A further validation strategy involves candidate. Moreover, the generalizability needed for the broad application of candidate biomarkers is challenged by (i) the heterogeneity of scanner, site and population effects, (ii) the neurobiological heterogeneity linked to main target syndromes and comorbidities of the ARMS and the recent-onset stages of psychoses, and (iii) the lack of technologies allowing for robust, yet adaptive interactions between computer-aided prognostic systems and human medical experts. To meet these challenges, machine learning methods are provided in order to translate candidate biomarkers into clinically viable neuroprognostic tools.

Complementary information sources for early detection: Along these lines, the present invention also focuses on the cross-centre applicability of neurocognitive and clinical prediction models. Previous studies achieved a good prediction of psychotic disorders by means of clinical, neurocognitive or combined analysis methods, including pattern recognition. In this regard, the augmentation of neuroimaging with complementary clinical information based on multivariate data fusion techniques will further increase the prediction accuracy and reliability of diagnostic tools for early recognition. Similarly, the integration of neuroimaging with genomic and metabolic data has proven a fruitful strategy for elucidating more quantifiable intermediate phenotypes of affective and non-affective psychoses.

Taken together, these findings suggest that multi-modal risk assessment tools combining neuroimaging and complementary data will to further enhance the prognostic accuracy of psychoses-related risk assessment tools.

Early detection in different healthcare settings: However, the individualised prediction of psychoses and poor functional outcomes will only be effective in reducing disease burden if aspect prognostic services are delivered to the main access points of mental health systems. Based on the current OECD report, these entry points are located in the primary health care sector: 75% of the 15% of European population seeking help for mental health-related problems consulted general practitioners, while 11% sought help from psychiatrists and another 14% from psychologists. Given these numbers and the fact that GPs typically do not receive the specialised training required for the early recognition of psychoses, it is evident that delayed diagnosis and treatment and hence disease chronicity not only result from the low predictive value of current clinical early detection instruments but also from systemic deficits within the mental healthcare infrastructure.

To overcome these deficits risk assessment services need to be delivered to care-givers at all levels of the mental healthcare system. Given the heterogeneity of the mental healthcare infrastructures in the EU, these services have to balance clinical needs against diagnostic constraints of the respective clinical situation in order to successfully deliver their products.

Figure 4:
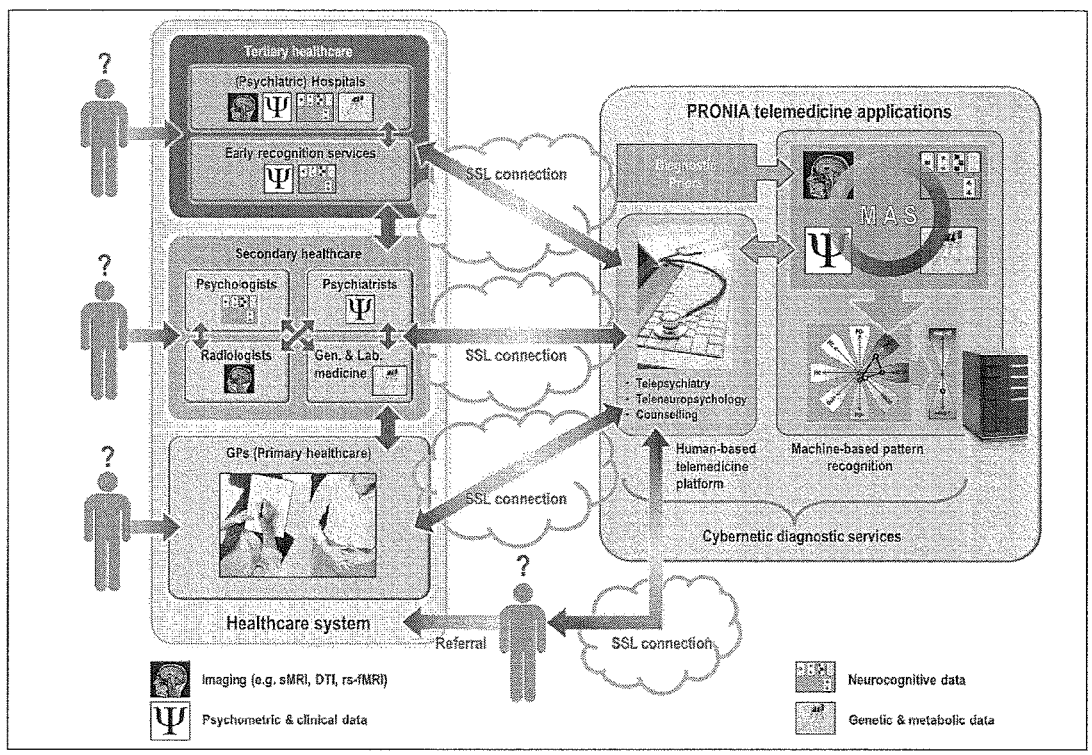
FIG. 4 depicts a preferred aspect of the present invention's telemedicine infrastructure and information flow.

These services need to be based on objective surrogate markers that are wrapped into deployment methods, which adaptively combine the relevant predictive signatures according to the given clinical situation. This situation includes the feasibility of diagnostic examinations as well as the pieces of diagnostic information already collated about the particular help-seeker. To achieve these goals, the present invention will implement flexible and accessible telemedicine infrastructures that provide communication interfaces between help-seekers, care-givers, mental health specialists and aspect risk assessment tools (FIG. 4). These interfaces will facilitate easy access to specialised risk quantification methods, and to specific forms of counselling and diagnostic support that adapt to the specialisation level of the requesting healthcare institution.

Hence, the present invention relates to a prognostic system that uses surrogate marker signatures, telemedicine and machine learning technology in order to create flexible and broadly deployable prognostic services. This effectively disseminates the present invention's prognostic services (PPS) to their target groups in the healthcare market: care-givers, the biopharmaceutical industry and research institutions. To realise these services, the present invention implements the following aspects:

1. Optimise the candidate imaging markers for a clinically reliable prediction and staging of psychoses by augmenting them with complementary patient data and generalising them across mental health services on the basis of CrOss-Centre, Multi-modal PAttern REcognition (COMPARE).
2. Provide surrogate markers for an individualised risk quantification by analysing brain imaging and complementary data with COMPARE in order to:
   a. Detect poor functional outcomes such as social and vocational exclusion in ROP patients, ARMS help-seekers and non-ARMS help-seekers with depressive syndromes,
   b. Model the impact of concomitant psychiatric conditions on predictions in aspects 1 and 2a that relate e.g. to the presence of depression, risk-conferring personality traits and substance abuse,
3. Monitor disease progression and remission across the at-risk and early stages of psychoses in order to dynamically refine predictions in 1, 2a & 2b by combining serial MRI scanning, neuropsychological, psychometric and metabolic assessments,
4. Disseminate and exploit these surrogate markers by delivering prognostic services to health service, research institutions and the biopharmaceutical industry through telemedicine-based communication.

The individualised risk assessment tools preferred for these goals are built and validated based on data, technology and results obtained in the following three the present modules according to the present invention:

Preferred MODULE I:

Generation of a large and representative database of 420 ROP patients, 420 ARMS help-seekers, 420 non-ARMS help-seekers with a recent-onset depression (ROD) and 420 healthy controls (HC) recruited across different catchment populations and healthcare systems (Tab. 1). These 1680 persons are uniformly characterised by neurobiological and behavioural measures that are highly relevant for surrogate marker generation, including structural and functional neuroimaging data, as well as clinical, genomic and metabolic information (see FIG. 2, section B 1.3 and WP01, 03-05 descriptions).

Tab. 1 further shows group-specific inclusion and exclusion criteria as well as general study exclusion criteria defined for participant recruitment across all study centres.

Participants for these four study groups are recruited at 6 European centres described in Tab. 2. Furthermore, our MRI surrogate markers are externally validated using the existing UoM database of 230 ROP, 220 ARMS (53 transitions) and >500 HC. In sum, the centres cover an ethnically diverse catchment population of over 7,600,000 people, spanning different healthcare systems and levels as detailed in Tab. 2.

This is a preferred power calculation of sample sizes: For the prediction of psychoses, a training sample of 200 ARMS individuals is required to achieve a sensitivity/specificity power of 0.90/1.0 ($\alpha$=0.05) in detecting a change in sensitivity & specificity from 0.5 to 0.7 based on a 27% transition rate over 18 months. For functional outcome prediction, 200 participants (FIG. 1) are needed to detect a change in sensitivity/specificity from 0.5 to 0.7 with a power of 0.86/1.0 and an average good outcome rate of 25% (socio-vocational & symptomatic recovery) in the ARMS and ROP. Thus, 315 (75% of 420) ARMS/ROP individuals are required to optimise and validate predictive models with nested, 5-fold cross-validation. The remaining participants are used for independent test set validation (25%).

Figure 2:
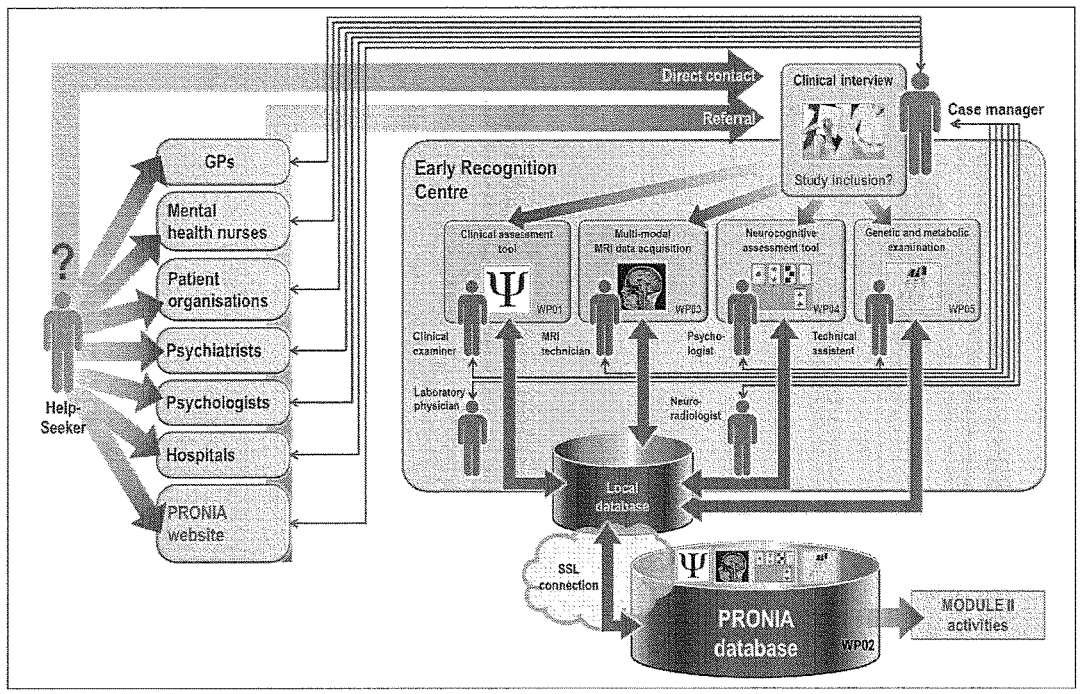

FIG. 2 depicts early recognition centre involved in MODULE I activities. The figure shows the diversity of study access pathways and personnel involved in case management as well as in the different baseline and follow-up examination modules. Results of examinations are communicated within feedback loops. Upon completion of each examination, data are stored in a local database and transmitted through an encrypted internet connection to the central database in accordance with the present invention.

Preferred MODULE II:

According to another preferred aspect of the invention robust machine learning methods capable of identifying, optimising and validating multi-modal surrogate marker signatures for adverse outcome prediction are implemented and applied to the data acquired. Cross-validation, leave-centre-out and test-set validations are preferably used to select surrogate markers for activities that generalize well across individuals, catchment populations and healthcare systems.

To achieve this preferred aspect of cross-centre prognostic generalization, the invention is preferably based upon tightly integrated system components, which are technically described in the following:

One preferred component comprises the following elements CrOss-Centre, Multi-modal PAttern REcognition (COMPARE): COMPARE is a data mining architecture capable of learning multi-modal surrogate marker signatures of psychosis-related risk by integrating different heterogeneous data sources (MRI, neurocognitive & clinical data and genetic & metabolic information). It consists of a two-layered machine learning framework devised to achieve high and generalizable predictive power across diverse clinical settings and at-risk populations (see FIG. 3). This requires algorithmic sequences that are robust against incomplete or spurious information, over-fitting, sample heterogeneity due to the presence of phenotypic variance (e.g. psychiatric co-morbidity, patient subgrouping) and irrelevant centre effects. The COMPARE architecture preferably implements the principle of stacked generalisation, in that layer 1 methods are first used to extract surrogate markers for risk-conferring clinical endpoints across different data sources. These endpoints are defined as categorical distinctions, ordinal stagings or continuous scores measuring an individual help-seekers loading on operationalized risk-conferring clinical axes: e.g. diagnostic criteria (e.g. HC vs. ROP, HC vs. ROD), clinical outcome (e.g. symptom remission vs. persistence), clinical course (e.g. unstable vs. stable symptoms), personality dimensions, poor premorbid adjustment and substance abuse.

Hence, the outputs of layer 1 machine learning predictors (e.g. support vector machines, SVM; relevance vector machines, RVM) on these layer 1 endpoints will be used to train meta classifiers and meta predictors of higher-order layer 2 endpoints: i.e. 'good vs. poor clinical outcome' (e.g. non-transition vs. transition to psychoses, episodic vs. chronic disease course) and 'good vs. poor functional outcome'. A step-wise overview of COMPARE is given in FIG. 3. It preferably comprises at least a plurality, more preferably all of the following steps:

I. Unimodal data acquisition, pre-processing and/or quality control: Pre-processing of data will be tailored to specific data modalities (e.g. segmentation, stereotactic normalisation of structural MR image). Step I processing sequences are governed by automatic quality control methods described as further below.

II. Optimisation of uniaxial, multi-modal similarity quantifiers: In case of high-dimensional data (e.g. MR images) the pre-processed information will first enter a feature generation module that employs different feature selection algorithms (e.g. margin-based feature selection methods) to rank features (e.g. voxels) according to their predictive relevance for given clinical target axes (e.g. classification of healthy controls vs. recent-onset patients). The obtained weighting will be applied to the input features by either determining an optimal cut-off threshold for feature selection (hard feature selection) or by computing the product images (weight vector*individual images; soft feature selection). Eventually, the weighted unimodal input spaces will be further processed with dimensionality reduction methods (e.g. Principal Component Analysis) to obtain compact sets of discriminative/predictive features. These features will be forwarded to unimodal machine learning algorithms, a.k.a. base learners (e.g. SVMs, RVMs) to detect optimally separating hyperplanes (OSH) for given clinical endpoints. These base learners produce decision scores that reflect a new test persons' geometric distance to the OSH. Hence, these derision scores quantify the individuals' similarity with respect to the learned classification categories. Finally, the fusion of different data modalities into a multi-modal similarity measure will be achieved by means of ensemble learning methods that form a committee-based decision rule through the integration of different uni-modal base learners. This ensemble-based data fusion strategy is robust against outliers and missing data as typically encountered in clinical real-world settings. The invention will use (1) diversity-inducing methods for ensemble construction (e.g. Generalised Ensemble Learning or DECORATE), and (2) boosting methods employed for data fusion (Learn++) in order to build the multi-modal similarity quantifiers.

III. Generation of a multi-axial, multi-modal profiling system: Step II will be repeated for different clinical endpoints as exemplified in FIG. 3. Then, the resulting uniaxial, multi-modal SVM similarity measures will be integrated into a multi-axial scoring system that allows the quantification of a test person's loading on multi-modal surrogate markers of risk-conferring target categories, including psychoses, depressive syndromes, substance abuse, personality traits and functional outcome. Thus, at the single-subject level step Ill will map psychosis-related neurobiological information to a new risk-conferring coordinate system that is spanned by the layer 1 endpoint prediction models.

IV. Generation of meta-classification systems from step III results: The study participants' multi-axial score profiles generated in step III will be used as input features for a second-level machine learning optimisation ("stacked generalisation"). Based e.g. on SVM or RVM algorithms, this optimisation consists of learning a prediction rule that maps from the subjects' loadings on the risk-conferring coordinate system (step III) to higher-order outcome targets (e.g. good vs. poor outcome). The rationale for developing these meta-classifiers or meta-predictors is the heterogeneity of neurobiological, neurocognitive and psychometric signatures, which is caused by variable psychiatric co-morbidities, clinical phenotypes and longitudinal courses within the help-seeking population. In this regard, these meta learners will be able to produce robust and generalizable decision rules for the psychoses and outcome prediction endpoints by identifying collinear and non-overlapping domains across the multi-axial score profiles.

To technically implement this system component, the invention will preferably use advanced ensemble learning methods, including generalized ensemble methods, stacked generalisation, heterogeneous ensemble methods, as well methods for diverse base learner selection and ensemble generation. These ensemble methods provide an enhanced performance, robustness and generalizability of predictive modelling. Furthermore, the invention will include novel SVM formulations that allow for the modelling of censored data (e.g. survival SVMs), thus allowing generating predictions in the time domain, e.g. facilitating the prediction of the time to transition in individual help-seekers. Finally, the invention will integrate semi-supervised and unsupervised machine learning methods into this system component, thus enabling the identification of low-level granularity structure in the uni-modal and multi-modal data spaces. This involves combining clustering methods (e.g. k-means clustering) with supervised algorithms (e.g. SVM) in order to implement local kernel machines which are capable of delineating heterogeneous neurobiological substrates of clinical endpoints at layers 1 and 2 of COMPARE.

Therefore, the clinically desired, single-subject identification of prodromal individuals requires this rate to be considerably improved in order to finally realise the ultimate purpose of early recognition: peaking prognostic power through the effective combination of single, potentially suboptimal information sources.

A need will be addressed by the present invention in that we will realise a modular technology transfer process by first collecting the multi-modal data basis (MODULE I) and then applying the machine learning to extract and validate surrogate markers for psychosis staging and outcome prediction (MODULE II).

Robust machine learning methods capable of identifying, optimising and validating multi-modal surrogate marker signatures for adverse outcome prediction are implemented and applied to MODULE I data. Cross-validation, leave-centre-out and test-set validation will be used to select surrogate markers for MODULE III activities that generalise well across individuals, catchment populations and healthcare systems (FIG. 3).

Figure 3:
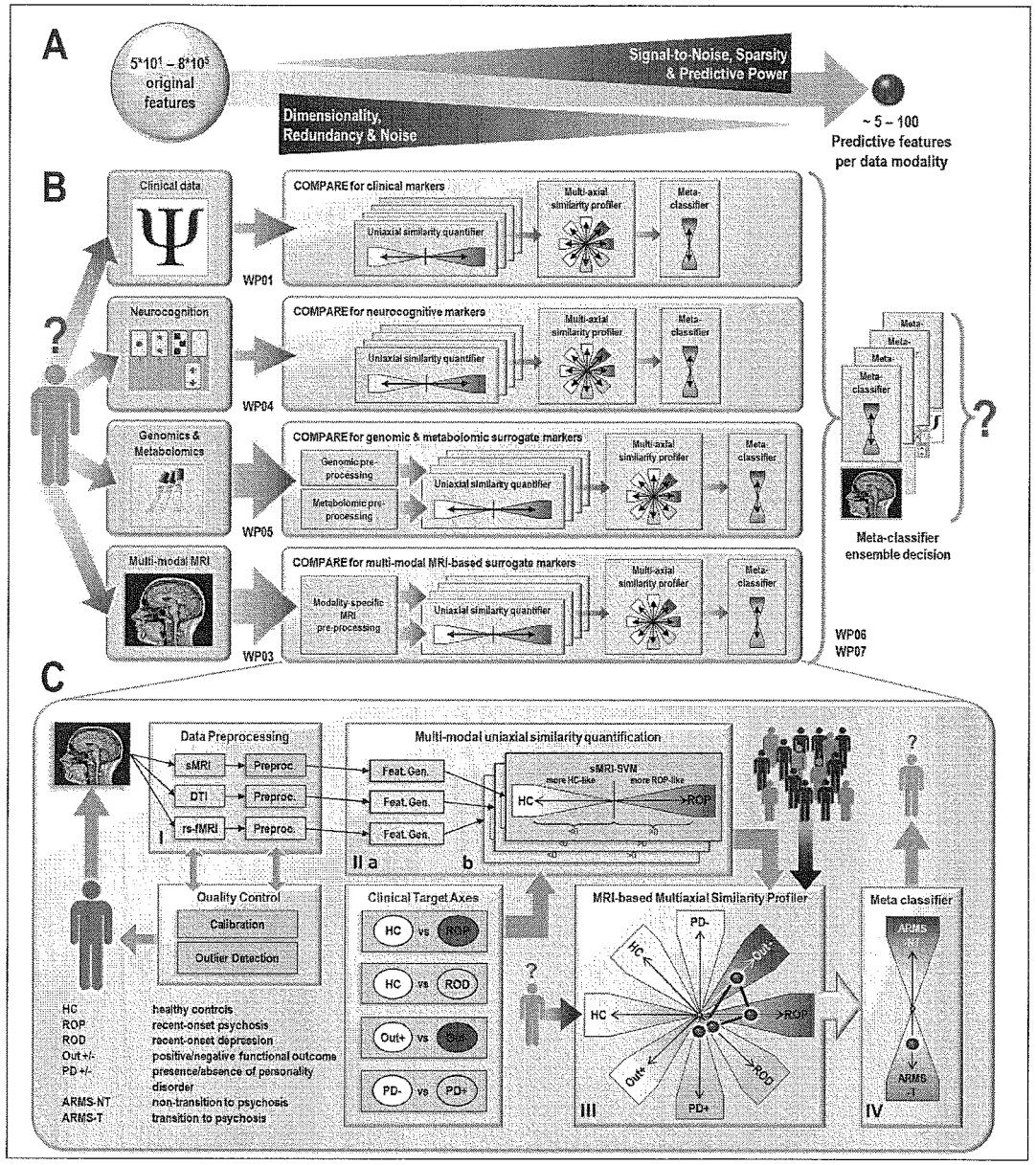
FIG. 3 is a graphical representation of the proposed COMPARE framework for surrogate marker generation.

FIG. 3 depicts a graphical representation of the proposed COMPARE framework for surrogate marker generation. Part A: During the data modality-specific information processing irrelevant information is removed from the original data resulting in highly predictive and sparse features for clinical endpoint prediction. Part B: This process is tailored to modality-specific COMPARE pipelines, generating predictive models that decompose the neurobiological and behavioural information into surrogate markers for different risk-conferring endpoints. This leads to modality-specific meta-classifiers that facilitate the individualised prediction of the present invention's main clinical endpoints. Based on ensemble learning principles, these modality-specific meta-classifiers are combined to a multi-modal outcome prediction. Part C: The COMPARE framework for MRI-based surrogate marker generation is presented in more detail. Step I: Multi-modal data acquisition and preferred pre-processing of different MRI modalities. A quality control system enhances data quality and automatically detects outliers during step I. Step IIa: Unimodal feature generation along clinical axes (e.g. HC vs. ROP classification), IIb: Optimisation of unimodal support vector machines; IIc: multi-modal similarity quantification. Step III: Repetition of II for different clinical axes and integration of resulting uniaxial similarity quantifiers into a multi-axial score profiler. Step IV: Score profiles are used to train a second-level (meta-classifier) to distinguish between individuals with a subsequent transition or non-transition to psychoses.

Preferred Automatic Quality Control Methods

The dissemination and commercial exploitation of surrogate markers for psychoses risk quantification can preferably be significantly enhanced by integrating automatic quality control systems into the prognostic and diagnostic processes. The main purpose of these systems is to act as intelligent sentinels in the modality-specific acquisition and processing of patient data, providing immediate feedback to operators if problems need to be addressed before information can be used for downstream prognostic evaluation. Preferably, such sentinel systems are used on the basis of one-class classification algorithms (e.g. one-class SVM) and have been successfully used to (i) detect faults in industrial processes, (ii) deliver control charts for effective multivariate process control, and (iii) assess the quality of microscopic imagery. With respect to the invention described here, these quality control systems can avoid bottlenecks and delays in the processing of prognostic information—particularly if quality assessment by human experts is unavailable or expensive. Hence, the implementation of such a system component enhances the reliability, generalization capacity and dissemination of the entire prognostic system across diverse healthcare settings. The quality control system described here consists of two preferred further aspects:

I. Outlier Detection During Data Acquisition:

For this purpose e.g. one-class SVM, Support Vector Data Description (SVDD) or k-Nearest Neighbour Data Description (kNNDD) methods are preferably used to train data modality-specific outlier detection systems using the raw data of healthy controls and help-seeking populations. These systems automatically generate outlier scores for given test person and provide feedback to the data acquisition operator if these scores exceed a given threshold.

II. Outlier Detection During Data Pre-Processing

By entering healthy controls' and help-seekers' pre-processed data into one-class machine learning models, data modality-specific outlier detection systems for pre-processed data evaluation will be preferably generated at critical steps of the pre-processing pipelines. These data modality- and pipeline-specific one-class models will be integrated into a data pre-processing control module that is capable of monitoring the quality of data pre-processing across the pipeline steps for the given modality. Optimal cutoff thresholds for outlier scores will be determined by quantifying the effect of different degrees and types of pre-processing failures on machine-learning predictors generated as part of above described preferred embodiment.

FIG. 6 exemplifies the preferred effect of described quality control modules on the MRI pre-processing pipeline: An MRI post hoc calibration tool and multi-step outlier detection system (sMRI pre-processing). After MRI data acquisition the MRI images are uploaded to the preferred prognostic system according to the present invention, where they are preferably first automatically processed by the MRI post hoc calibration tools to minimise scanner-induced variance in the data. Then, the calibrated images are forwarded to the modality-specific pre-processing pipeline (in the preferred case sMRI). After each processing step, the outlier detection system assesses image quality with respect to a learned reference data distribution (e.g. based on one-class SVM) and either approves or rejects further processing.

In the latter case the case manager and local MRI technician are informed about the processing failure of the system.

Multi-Agent System (MAS): According to a further preferred embodiment of the present invention performance of telemedicine applications could be substantially enhanced on the basis of advanced computational bioinformatics methods, formulated as adaptive Multi-Agent Systems (MAS). In this regard, the preferred embodiment of the invention is fully in keeping with the frameworks for imaging-based CAD systems, which involve the combination of high-throughput technologies for the processing of high-dimensional patient data with human expert knowledge and process flow technologies. More specifically, the prognostic system built upon the invention will consist of a modular architecture that distributes its functionality to a set of cooperating elements orchestrated by a central process supervisor (see also FIG. 5).

These preferred cooperation elements are further described in Tab. 3, the invention's MAS component will consist of interactive and collaborative software elements, termed agents, which query client and environmental information, prepare modality-specific data, provide predictions for given help-seekers and report results to clients. Accordingly, these agents encapsulate or interface with surrogate marker models provided by System Component 1, outlier detection systems provided by System Component 2 and the telemedicine methods developed in System Component 4. Upon activation, these agents are co-ordinated by a diagnostic workflow engine (supervisor program) that is capable of creating and personalising diagnostic streams by:

i. Initialising agents needed for a given diagnostic task (e.g. clinical evaluation), comprising agents for data acquisition, processing and result reporting.

ii. Forming modality-specific diagnostic layers that have a built-in logic for organising agents into information processing streams (e.g. acquisition, calibration, segmentation, normalisation and outcome prediction of structural MRI data, monitored by a data quality control agent).

iii. Adapting the agent selection process by integrating the following process variables;

The prognostic outcome (post-test probability) so far achieved by the diagnostic stream, The multi-axial risk-conferring profile of the help-seeker, and/or The diagnostic constraints of given clinical situations (e.g. costs, invasiveness, duration and quality of examinations).

This adaptation process itself is governed by a machine learning system that will be trained to predict the optimally achievable, prognostic post-test probability by choosing the diagnostic examination (e.g. neurocognitive test, MRI scan, genetic test, metabolic assay) which maximizes the gain of diagnostic certainty in given test person. The supervisor program at the core of the MAS will be implemented e.g. as a Markov Random Field model or alternatively as a neural network which are trained to predict sequential diagnostic steps which together maximise prognostic performance and reliability. These diagnostic streams are adaptive in that the subsequent diagnostic steps within the stream are sensitive to the conjoint post-test probabilities of the previous steps. By running extensive simulations of possible diagnostic streams, the machine learning method or algorithm will be trained to predict the post-test probability achievable in a given clinical situation by a given diagnostic examination as is shown in FIG. 7.

FIG. 7 depicts a possible diagnostic stream generated by the Markov Random Field (MRF) approach and leads to a successive increase in prediction accuracy through the ensemble-based combination of clinical, MRI-based and neurocognitive predictors. These predictors add complementary information to the overall ensemble prediction, thus reducing the overall uncertainy of the prognostic system. Through integration of diagnostic priors into the path selection, the MRF is capable of adapting to the clinical situation of the given help-seeker.

The generation of diagnostic streams through the invention's MAS component is exemplified in FIG. 5 which exemplifies steps of a diagnostic stream within the present invention's tentative multi-agent system. The figure describes the prognostic process within the present invention's MAS and between the MAS and given clients: A help-seeking person contacts the MAS through a clinical online interface that provide a self-rating assessment and automatic evaluation. If caseness criteria are positive, the person is referred to a medical case manager (e.g. psychiatrist). The case manager activates the MAS by selecting the clinical outcome question. In turn, the MAS supervisor program queries clinical agents from the agent database, which are automatically assembled into a clinical diagnostic layer. Then, both case manager and help-seeker provide clinical/psychometric data to the clinical assessment interface. These data are forwarded to a clinical quality control module that evaluates data integrity and quality and in turn passes the data to the clinical COMPARE agent (see also FIG. 3). Based on its trained machine learning models the COMPARE agent generates the multi-axial risk-conferring signature of the help-seeker and passes it to the clinical meta-classifier. Additionally, the results of these computations are fed back to the clinical assessment agent, which reports them to case manager via the General IO interface of the MAS. The meta-classifier computes the individual's risk for a transition to psychoses within the next 18 months and returns this prediction to the supervisor, which in turn provides feedback to the case manager via the General IO interface. Furthermore, based on this prediction, the multi-axial clinical profile and the current diagnostic priors, the supervisor computes the increase of prognostic certainty obtained from an additional examination in one of the remaining diagnostic modalities (MRI, neurocognition, genetic and metabolic data). In the given clinical situation, it concludes that MRI provides the highest increase in prognostic certainty. The case manager is informed and suggests an MRI examination to the help-seeking individual. After this examination, the MRI scans are uploaded to the MAS, where the supervisor recruits the MRI-based diagnostic layer from the agent database. MRI-based COMPARE and meta-classifier agents are selected to maximise complementarity with respect to the previous predictions. The data flow within this layer involves MRI calibration methods, quality control methods (see System Component 2), pre-processing pipelines and COMPARE evaluation (see System Component 1) terminating in the prediction generated by the MRI-based meta-classifier, which is returned to the supervisor. The supervisor integrates the clinical and MRI-based predictions and provides feedback to the case manager with respect to the present invention's multi-modal prediction.

Preferred MODULE III:

First, MODULE II surrogate markers, quality control tools and web-based interface technologies can I be integrated into the prognostic devices and services that are adapted and delivered to diverse healthcare settings and remote areas through easily accessible telemedicine platforms (FIG. 4).

FIG. 4: the present invention's telemedicine infrastructure. The present invention prognostic system consists of human telemedicine and machine-based neuroprognostic modules: Telepsychiatric and teleneurocognitive platforms link care-givers and help-seekers with registered and trained medical experts who assess required caseness criteria as well as the clinical and neurocognitive items. These experts interact with the machine-based prognostic module to control the entire examination and evaluation process. Machine-based pattern recognition is organised by a multi-agent system (MAS) that adaptively combines the multi-modal surrogate marker signatures based on the clinical question at hand, the neurobiological/behavioural signature of the given help-seeker and the respective diagnostic settings. The present invention prognostic system is connected to registered healthcare services over the internet, and thus disseminates and guides neuroprognostic decision making depending on the geographic location of help-seekers and care-givers.

Preferred Aspect 1: Optimisation of Candidate Biomarkers of Psychoses Based on COMPARE According to the present invention multivariate analysis methods are employed to overcome these shortcomings of the current state-of-the-art as described before. Importantly, the feasibility of an imaging-based prediction of psychoses in two independent ARMS populations have been demonstrated, achieving prediction accuracies of 84%-88% by means of cross-validated support vector machine classification.

Furthermore, an accurate staging of psychoses into prodromal and recent-onset states of the disease based on cross-validated MRI-based pattern classification is achieved.

The present invention leads to accurate neurodiagnostic tools for psychoses prediction that will enable the effective individualised disease staging of psychoses. In this regard, the modular work flow preferably enables that compact non-redundant surrogate marker signatures will be extracted and validated from a multi-site and multi-modal study database. These signatures are confined to features that conjointly maximise prediction performance, minimise information redundancy and optimise robustness against site-related confounds. Furthermore, by building these surrogate markers upon our COMPARE framework, we will generate prognostic tools that operate reliably under clinical real-world conditions, including missing information, as well as phenotypic, neurobiological and population based diversity. Moreover, the present invention will extend the predictive capabilities of our candidate markers to the single-subject estimation of the time to transition based on survival support vector machines. This optimisation provides crucial information to the clinical practitioner in that it will enable the personalisation of therapeutic measures according to an imminent risk of disease transition.

Hence, this translational strategy provides firm grounds for diagnostic and therapeutic decisions early in the course of psychoses, paving the way for personalised care and prevention: e.g. the prescription of antipsychotic treatment only in cases with the highest risk of unfavourable clinical outcomes. This will help to minimise medication side effects in persons with lower disease vulnerability, while maximising therapeutic benefit though the choice of less harmful interventions like cognitive-behavioural therapy. Furthermore, the widespread deployment of these neuroprognostic services through easily accessible and broadly available telemedicine applications (FIG. 4) will reduce the time lag between the onset of symptoms and the commencement of treatment. Taken together, the optimisation, validation and dissemination of these neuroprognostic tools will lead to a major clinical breakthrough in the early recognition and prevention of psychoses, in that these steps will translate current research-based early detection strategies into health services dedicated to the management of early psychosis.

Preferred Aspect 2: New Surrogate Markers for the Individualised Risk Quantification of Psychoses Preferred aspect 2a—Prediction of functional outcome: To date, early recognition strategies focus on the prediction of psychosis. However, recent research indicates that a considerable proportion of help-seekers show enduring social and vocational dysfunction irrespective of a subsequent disease transition or psychiatric diagnosis.

This impairment means that these help-seekers create a large, yet unexplored socioeconomic harden. This burden can only be reduced with neuroprognostic risk assessment instruments that reliably pinpoint those persons at the highest risk for adverse functional outcomes. In this regard, it is suggested that ARMS non-transition (ARMS-NT) individuals differ neuroanatomically from both prodromal patients and health controls.

Furthermore, for the first time it is possible that these ARMS-NT individuals could be distinguished from healthy controls by using neuroanatomical and neurocognitive pattern classification, with cross-validated accuracies ranging from 67% to 86%. This variability is possibly associated with neurobiological heterogeneity linked to diverse clinical and functional outcomes, ranging from a complete symptomatic and functional remission to enduring subthreshold psychoses and functional impairment in different subgroups of ARMS-NT individuals.

Similarly, the disease course following ROP varies considerably from complete recovery to severe long-lasting impairment. Therefore, it is of utmost importance to develop individualised predictors of functional outcome in the early stages of established illnesses. These predictors could aid in allocating therapeutic resources and providing specific treatment to patients at the greatest risk for disabling disease outcomes. Despite initial promising results, it is still unknown whether functional outcome predictors could (i) operate across different stages of psychoses, (ii) be further enhanced by the complementary integration of different data modalities, and (iii) generalise their prediction performance across different healthcare settings.

Preferred aspect 2b—Modelling of risk-conferring psychiatric co-morbidities: The clinical heterogeneity of psychoses is fuelled by the varying presence of psychiatric comorbidities, for which the disease seems to be a strongly predisposing factor.

Recent studies, showed that particularly comorbid mood, anxiety and substance abuse disorders extend to the ARMS for psychoses. These concomitant psychiatric conditions significantly increase the risk for adverse outcomes in this critical phase of the disease process.

Furthermore, this clinical heterogeneity, which spans different disease stages, may be linked to considerable neurobiological diversity, thus challenging the performance, reliability and generalisation capacity of neuroprognostic methods. Importantly, these methods have so far been based upon a one-dimensional conceptualisation of the ARMS, thus not accounting for the risk-related variance associated with different psychiatric comorbidities and diagnostic outcomes.

Preferred aspect 2c—Neuromonitoring of disease progression and remission: Previous studies demonstrated progressive neurocognitive and neuroanatomical changes underlying emerging psychoses.

These group-level findings point to neurobiological trajectories of illness progression that could be individually predicted early on during disease development. Prior, it has been unknown whether the variability of clinical courses is paralleled by neuroanatomical, neurocognitive and metabolic changes at the single-subject level. Furthermore, it can be elucidated whether this information could (i) be used to accurately determine the 'position' of single at-risk persons on these multi-modal disease trajectories, (ii) be employed to improve the prognostic performance of models implementing the present invention's aspects 1, 2a and 2b, and (iii) enhance and adapt preventive therapy on the basis of a regularly updated 'neurostatus' on the progression or remission of the disease processes.

This progress beyond the art will lead to surrogate markers that are robust against the phenotypic heterogeneity of early psychoses caused by concomitant psychiatric conditions and variable clinical courses. On the other hand, these surrogate markers will provide a higher level of flexibility and hence personalisation of prognosis and therapy to the given help-seeker. Therefore, realising robustness and flexibility to phenotypic and neurobiological diversity may lead to a major clinical breakthrough as both properties are critical pre-requisites for the successful dissemination of objective risk quantification and indicated prevention strategies.

The present invention's MODULE II activities provides an integrative solution to these aspects in that we will shift from a one-dimensional conceptualisation of early psychoses toward a more flexible modelling of risk targets at different stages of the disease. This progress beyond the state-of-the-art requires a two-layered machine learning framework that (i) successfully decomposes the neurobiological profile of a given test person with respect to a multi-dimensional panel of risk-associated clinical endpoints (FIG. 3), and (ii) maps different clusters of these profiles present in the help-seeking population to the two main targets of early recognition, i.e. prediction of adverse clinical and functional outcomes. By means of COMPARE (FIG. 3), it is possible to generate multi-modal signatures that explicitly describe the phenotypic and neurobiological diversity underlying these two target endpoints. This will significantly reduce the prediction error caused by the direct search for signatures of high-level, heterogeneous endpoints, such as 'transition vs. non-transition'. Furthermore, COMPARE can be easily extended to integrate cross-sectional and longitudinal data from different data sources (e.g. serial MRI, repeated neurocognitive assessments and time courses of metabolic changes). Thus, the monitoring of the neurobiological and behavioural trajectories associated with different clinical and functional outcomes will further reduce prognostic uncertainty in our neuroprognostic tools. This will enable the regular appraisal of the at-risk individuals' 'neurostatus', thus enabling care-givers to adjust their therapeutic strategies to their patients' dynamic clinical and neurobiological changes.

According to the present invention surrogate markers are provided that are robust against the phenotypic heterogeneity of early psychoses caused by concomitant psychiatric conditions and variable clinical courses. On the other hand, these surrogate markers will provide a higher level of flexibility and hence personalisation of prognosis and therapy to the given help-seeker. Therefore, realising robustness and flexibility to phenotypic and neurobiological diversity may lead to a major clinical breakthrough as both properties are critical pre-requisites for the successful dissemination of aspect risk quantification and indicated prevention strategies.

Aspect 3: Dissemination and Commercial Exploitation of Neuroprognostic Services

Up to now, health services dedicated to the early recognition of psychoses have strived to improve the prevention of these illnesses by enabling research into the clinical, neurocognitive and neurobiological phenotypes of disease susceptibility. However, this research strategy has so far not lead to significant and sustainable benefits at the personal and socioeconomic level, although intervention studies have demonstrated that treatment commencing early in the disease course may improve outcomes and hence reduce the immense costs of the established illness.

The first reason thereof is the lacking translation of scientific evidence into practical clinical tools facilitating diagnostic decision making early in the course of psychoses. This translation cannot be achieved without the integration of surrogate marker detection systems, data quality control systems and human-machine interfaces, which conjointly increase the accuracy, reliability and flexibility of prognostic tools. However, these three elements are currently unavailable for the early recognition of psychoses. In consequence, there is also a lack of infrastructure and entrepreneurial activity propelling the dissemination of such tools to help-seekers and care-givers at the routine clinical level.

Furthermore, there are presently no certified prognostic services.

The present invention will move beyond this clinical state-of-the-art by realising its MODULE III work packages (see FIG. 4): first, quality control methods are developed for neuroimaging that facilitate an improved data acquisition quality and integrity as crucial pre-requisites for clinically viable neuroprognostic applications. More specifically, these methods will consist of post hoc scanner calibration methods that allow new scanners to be harmonised with original scanner database without changing their data acquisition parameters. Furthermore, we will implement outlier detection methods based on machine learning techniques that will enable the monitoring of MRI data quality during the data acquisition and processing steps. Both methods will facilitate the dissemination and commercial exploitation of MRI-based prognostic services.

Second, data acquisition, pre-processing, quality control and prognostic mechanisms are preferably integrated into a flexible and reliable medical prognosis architecture. This architecture will consist of a multi-agent System (MAS) that encapsulates these mechanisms into expert software programs (agents), which adaptively combine to create diagnostic streams for given help-seekers under the constraints of the given mental healthcare setting (FIG. 5). Intelligent MAS have been recently proposed for streamlining medical decision making, reducing medical error in imaging and providing high-quality telemedicine services to remote areas with scarce medical resources.

Within these frameworks, the MAS proposed by the present invention will be embedded into a telemedicine application that interfaces with care-givers, help-seekers and medical experts, thus facilitating mutual control of the evolving diagnostic stream for a given help-seeking person (FIG. 4).

This progress will create adaptive prognostic services that can be delivered to diverse mental healthcare settings. Importantly, these services will not only consist of machine-based neuroprognostic tools, but also incorporate user-friendly interfaces for self-assessment, telepsychiatric exploration, telecognitive evaluation and expert collaboration that will interact with the neuroprognostic systems.

The state-of-the-art is further preferably overcome by testing the present invention's prognostic services with the most conservative method available, i.e. external validation. This validation uses multi-modal datasets of help-seekers and healthy controls, who will be recruited from two geographically very distant catchment areas (Melbourne, Munich) in parallel to and without the quality assurance (QA) measures of the main study. Then, test cases are generated from these multi-modal data, which is presented to telemedicine-based services in order to externally validate the present invention's prognostic performance under different simulated clinical conditions. This allows to estimate the flexibility, reliability and efficacy of the entire risk quantification system. In addition, we will externally validate our MRI-based surrogate markers using our Australian existing MRI database, which currently contains the data of 230 ROP, 220 ARMS and >500 HC individuals. By achieving these validation goals, the medical and commercial risks of its prognostic products will be effectively controlled.

Taken together, the present invention will create thoroughly validated and easily deployable instruments for multi-dimensional risk assessment in pre-clinical and early psychoses. Due to their availability at the main entry points of the mental healthcare systems, these tools significantly expand the catchment population of early recognition, moving it beyond the highly specialised clinical centres. Hence, they promote the goals of the European Pact for Mental Health, particularly those identified in the areas 'mental health in youth and education' and 'prevention of depression and suicide'. Finally, the identification and validation of neurobiological risk signatures, which can be monitored throughout the clinical course, will reinvigorate the pharmaceutical industry's interest in developing novel preventive compounds.

FIG. 5 visualizes preferred steps of a diagnostic stream within the present invention's tentative multi-agent system. The figure describes the prognostic process within the present invention's MAS and between the MAS and given clients: A help-seeking person contacts the MAS through a clinical online interface that provide a self-rating assessment and automatic evaluation. If caseness criteria are positive, the person is referred to a medical case manager (e.g. psychiatrist). The case manager activates the MAS by selecting the clinical outcome question. In turn, the MAS supervisor program queries clinical agents from the agent database, which are automatically assembled into a clinical diagnostic layer. Then, both case manager and help-seeker provide clinical/psychometric data to the clinical assessment interface. These data are forwarded to a clinical quality control module that evaluates data integrity and quality and in turn passes the data to the clinical COMPARE agent (see also FIG. 3). Based on its trained machine learning models the COMPARE agent generates the multi-axial risk-conferring signature of the help-seeker and passes it to the clinical meta-classifier. Additionally, the results of these computations are fed back to the clinical assessment agent, which reports them to case manager via the General IO interface of the MAS. The meta-classifier computes the individual's risk for a transition to psychoses within the next 18 months and returns this prediction to the supervisor, which in turn provides feedback to the case manager via the General IO interface. Furthermore, based on this prediction, the multi-axial clinical profile and the current diagnostic priors, the supervisor computes the increase of prognostic certainty obtained from an additional examination in one of the remaining diagnostic modalities (MRI, neurocognition, genetic and metabolic data). In the given clinical situation, it concludes that MRI provides the highest increase in prognostic certainty. The case manager is informed and suggests an MRI examination to the help-seeking individual. After this examination, the MRI scans are uploaded to the MAS, where the supervisor recruits the MRI-based diagnostic layer from the agent database. MRI-based COMPARE and meta-classifier agents are selected to maximise complementarity with respect to the previous predictions. The data flow within this layer (MRI calibration, quality control, pre-processing, COMPARE evaluation) ends with the prediction by the MRI-based meta-classifier, which is returned to the supervisor. The supervisor integrates the clinical and MRI-based predictions and provides feedback to the case manager with respect to the present invention's multi-modal prediction.

The present invention aims at predicting psychosis or subsequent disease courses in single at-risk individuals using MRI, neurocognitive and/or clinical data. So far, the highest positive likelihood ratios achieved by MRI-based predictors of transition to psychosis ranged between 10.7 and 6.5. Disease course prediction based on MRI and pattern recognition methods reached a 71% sensitivity and 68% specificity in distinguishing between first-episode patients with subsequent continuous vs. episodic disease courses. These results were obtained in small samples, using different methodologies and without independent test data validation. Hence, the present invention will enable the predictive performances of these baseline neuroimaging studies and allow generalization to larger at-risk populations recruited across different healthcare systems and analysed by means of a standardized machine-learning framework. Furthermore, the present invention will evaluate which combination(s) of different MRI protocols provide the most reliable and accurate prediction results across different centres and at-risk groups, while minimising the diagnostic load on the individual help-seeker.

Similarly, studies using baseline neurocognitive performance measures to predict a later transition to psychosis reported prognostic accuracies of 80% in combination with clinical information. However, these studies did neither employ thorough cross-validation or external validation tests in order to evaluate the generalizability of their predictive models to new at-risk populations. Recently, cross-validated neurocognitive pattern classification achieved an accuracy of 77.5% in predicting psychosis in single ARMS individuals. As with the other studies, this encouraging finding is limited by the small sample size problem, which makes it difficult to estimate its generalizability. Therefore, the present invention will collate and analyse a multi-centre database covering diverse catchment population in order to thoroughly evaluate the real world generalisation capacity of neurocognitive disease predictors. During this data analysis process, the present invention determines the most compact set(s) of neurocognitive variables that maximise prediction performance and cross-centre applicability of these predictors, while reducing the duration of neuropsychological testing.

Finally, clinical predictors of psychosis have been recently provided by two investigations. These studies reported accuracies between 68% and 83.3% in predicting a later transition to psychosis. Because of the larger multi-centre datasets examined in these studies, these results are robust. Hence, the present invention will both determine optimal sets of clinical predictors and benchmark the applicability of already proposed as well as newly obtained clinical prediction models to new at-risk persons by employing increasingly conservative methods of out-of-training generalizability estimation.

Beyond the baseline summarised above, the (1) genetic and/or metabolic prediction models could enable the single-subject risk quantification of persons at-risk of psychosis-related outcomes, (2) multi-modal predictors mixing heterogeneous data sources (MRI, neurocognitive, clinical and geno-metabolic information) could be employed for an individualised risk stratification that outperforms uni-modal prognostic models, (3) different diagnostic methods and derived prognostic models could be tailored to the individual at-risk person in a given diagnostic environment, and (4) whether the knowledge generated in (1)-(3) could be translated into adaptive prognostic services that could be disseminated to different healthcare systems and levels.

The performance of the subject-matter according to the present invention in achieving its aspects is measured by the indicators listed below. These are divided into 3 groups: (1) Quantitative indicators measuring the performance of subject recruitment, baseline and follow-up examinations per recruiting centre, study group and data modality, (2) Qualitative indicators describing methods implemented in the present invention (e.g. software functionalities, analysis strategies), and (3) Quantitative indicators measuring the performance of surrogate markers in predicting the present invention's target endpoints in single out-of-training subjects. These measures are computed using increasingly conservative estimates of generalisability, consisting of pooled cross-validation, leave-centre-out cross-validation, independent test validation and external validation. Performance measures will be reported along with (a) the underlying training and test sample sizes, (b) eventually performance changes compared to the previous evaluation periods and (c) the type of validation method employed.

FIG. 8 exemplifies a voxel probability map of reliable contributions to the ARMS-NT versus ARMS-T decision boundary. Voxels with a probability of >50% were overlaid on the single subject Montreal Neurological Institute template using the MRIcron software package (http://www.sph.sc.edu/comd/rorden/mricron/).

FIG. 9 shows on the left a comparison of Kaplan-Meier survival curves in ARMS individuals with a low, intermediate, and high neuroanatomical risk level. Vertical lines indicate censoring events, while steps represent transition events in the ARMS population over the follow-up period. On the right a plot analysis of psychosis-free survival times across these three neuroanatomical risk levels is shown. The latter two figures show ARMS at-risk mental states.

TABLE 1

| Group | Group inclusion | Group exclusion | Study exclusion |
|---|---|---|---|
| ROP | EITHER (i) transition criteria defined by Yung et al.[72] OR (ii) ICD-10: F20.x, F22.x, F23.x, F25.x, F28, F29, F31.2, F32.3 | Duration of psychoses > 12 months Duration of antipsychotic medication > 3 months | Age < 15 OR > 40 IQ < 70 Current or past head trauma |
| ARMS | EITHER (i) CAARMS criteria OR (ii) SPI-A criteria OR (iii) GAF reduction ≥ 30% and positive family history of psychoses OR (iv) GAF reduction ≥ 30% and criteria for schizotypia (ICD-10: F21) | Inclusion criteria for recent-onset psychoses | Current or past neurological illness Current or past serious medical or surgical illness |
| ROD | (i) ICD-10 F32.x | Inclusion criteria for ROP and ARMS Duration of depressive episode > 12 months | affecting CNS function ICD-10: |
| HC | | Personal history of affective or non-affective psychoses or other psychiatric conditions Family history of psychoses (1° relatives) | Dependence syndrome (F1x.24/ F1x.25) |

TABLE 2

| Participant Short Name | Catchment population | Screening pop./year | No. ROP/year | No. ARMS/year | No. ROD/year | No. Scans/week | Scanner hardware |
|---|---|---|---|---|---|---|---|
| UNIBAS/UPK | 500,000 | 200 | 50 | 25 | 50 | 3 | Siemens 3T |
| Uni BHAM | 1,200,000 | — | 200 | 60 | 400 | 8 | Philips 3T |
| UKK | 1,000,000 | 600 | 25 | 25 | 50 | 2-3 | Philips 3T |
| UTU | 300,000 | 2,000 | 60 | 40 | 70 | 2-4 | Philips 3T |
| LMU | 1,300,000 | 700 | 100 | 30 | 150 | 4 | Siemens 3T |
| Uni Udine | 600,000 | 500 | 25 | 25 | 50 | 2-3 | Philips 1.5T |
| Total (main study) | 4,900,000 | 4,000 | 460 | 205 | 770 | 21-25 | |
| UoM | 1,500,000 | 600 | 40 | 40 | 50 | 4 | Siemens/GE 3T |
| Munich area | 1,200,000 | — | 150 | — | 300 | 10 | Siemens/GE 3T |
| Total | 7,600,000 | 4,600 | 650 | 245 | 1120 | 35-39 | |

TABLE 3

| Component Name | 1.1. Component type | 1.2. Component function |
|---|---|---|
| 1.3. Telepsychiatric and telecognitive assessment tools | 1.4. Interface | 1.5. Web-based tools with video-conferencing and standardised behavioural data acquisition |
| 1.6. Counselling tools | 1.7. Interface | 1.8. Web-based tools with video-conferencing capabilities allowing for remote care-giver interactions |
| 1.9. Diagnostic priors | 1.10. Interface | 1.11. Web-based tool for the specification of diagnostic constraints in given clinical situation |
| 1.12. Agent database | 1.13. Database | 1.14. Database storing and providing components for diagnostic information processing |
| 1.15. Surrogate marker signatures | 1.16. Predictor | 1.17. Prediction of functional outcomes by either direct modelling or two-layer modelling (see COMPARE framework in WP02) of clinical/functional outcomes |
| 1.18. Pre-processing pipelines | 1.19. Data preparation | 1.20. Modality-specific pre-processing of information (e.g. segmentation and normalisation of MRI images or genomic characterisation of blood samples) |
| 1.21. Quality control methods | 1.22. Data preparation | 1.23. Modality-specific analysis of deviation from reference database |
| 1.24. Feedback systems | 1.25. Interface | 1.26. Modality-specific and multi-modal agents returning critical processing information (e.g. outcome prediction) to the client |
| 1.27. Diagnostic layers | 1.28. Containers | 1.29. Modality-specific sequential organisation of components into information processing streams for given data source |
| 1.30. Supervisor | 1.31. Process control | 1.32. Core functionality of PRONIA's prognostic streams generating and adapting diagnostic streams on the basis of the input and output information of agents |
| 1.33. Evaluation database | 1.34. Database | 1.35. Database storage of process information for every clinical case |

TABLE 4

| Variable | Low Risk | Intermediate Risk | High Risk | $\chi^2$ (P) |
|---|---|---|---|---|
| Psychosis-free survival time: median (95% CI; range) [mo] | 50.5 (37.4-54.0; 75.3) | 48.5 (26.9-49.7; 85.1) | 4.9 (6.2-24.3; 75.6) | 17.33 (<.001) |
| Transition rate (95% CI) [%] | 8.3 (3.3-30.8) | 37.5 (21.1-57.4) | 87.5 (68.2-97.3) | 29.04 (<.001) |
| Pairwise log-rank tests [$\chi^2$ (P)] | | | | |
| Low risk | — | 5.38 (.020) | 31.60 (<.001) | — |
| Intermediate risk | 5.38 (0.020) | — | 12.96 (<.001) | — |
| Center composition of risk groups [N (%)] | | | | |
| Munich | 10 (40.0) | 12 (50) | 14 (58.3%) | 1.65 (.469) |
| Basel | 15 (60.0) | 12 (50) | 10 (41.7%) | |

The invention claimed is:

1. A method for detecting psychosis prodrome comprising:
   a. automatically constructing at least one risk quantification or classification system based upon brain images and data mining;
   b. predicting at least one psychosis at a single subject level, by learning at least one neuroanatomical feature;
   c. computing an unbiased estimate of an expected diagnostic accuracy;
   d. generating and processing uni-modal data with a dimensionality reduction method;
   e. combining a diverse plurality of uni-modal base learners with an ensemble learning process across different data domains.

2. The method according to claim 1, further comprising, extracting specific surrogate markers by multi-modal data acquisition and/or categorizing and/or quantifying the surrogate markers by a multi-axial scoring system for said at least one risk quantification or classification system(s).

3. The method according to claim 1, further comprising controlling the data at different operations of a pre-processing and a risk-quantification process to detect outliers, by determining cut-off thresholds.

4. The method according to claim 1, further comprising optimizing the uni-modal data based upon the data acquired and/or the further operation of quantifying one or more similarity and/or dissimilarity between the multi-modal data and the uni-modal data.

5. The method according to claim 4, wherein the multi-modal data similarity is carried out by means of committee-based decision rule by the combination plurality of uni-modal base learners.

6. The method according to claim 2, wherein the operation of multi-modal data acquisition is performed by one or more feature selection methods, which are margin-based feature selection methods, to rank features, including voxels, according to relevance of the features for the markers.

7. The method according to claim 2, wherein the operation of detecting and eliminating outliers is performed for the first and/or a second risk quantification or classification system(s) by one-class SVM, Support Vector Data Description (SVDD) and/or k-Nearest Neighbour Data Description (kNNDD) methods.

8. A method for detecting an adaptive pattern recognition for psychosis risk modeling comprising:
   a. automatically constructing at least one risk quantification or classification system based upon brain images and data mining;
   b. automatically generating a second risk quantification or classification system based upon genomic and/or metabolomics information and data mining; and
   c. processing the first and second risk quantification or classification systems by data mining computing so as to create a meta-level risk quantification data to automatically quantify psychosis risk at a single subject level;
   wherein the multi-modal data similarity is carried out by means of committee-based decision rule by an integration of a plurality of uni-modal base learners;
   wherein the unimodal data are further processed with dimensionality reduction methods including a principal component analysis adapted to obtain compact sets of discriminative and/or predictive data and/or wherein sets of discriminative and/or predictive data is forwarded to uni-modal machine learning methods to detect separating hyperplanes (OSH) for psychosis classifications or patterns and to provide decision scores according to a geometric distance to a hyperplane (OSH) and/or to a respective classification.

9. The method according to claim 2, wherein the multi-axial scoring system further performs a second-level machine learning optimization, including at least one advanced ensemble learning method, comprising generalized ensemble methods, stacked generalization, heterogeneous ensemble methods, stacked generalization, heterogeneous ensemble methods, and at least one method for diverse base learner selection and ensemble generation, comprising a learning of one or more prediction rules.

10. A method according to claim 1, wherein at least one post hoc scanner calibration method is employed for the brain images which is adapted to minimize scanner-induced variance and/or harmonize new scanners with already used scanners and/or calibrated brain images are forwarded to modality specific pre-processing, including sMRI.

11. A method according to claim 2, comprising integrating a plurality of specific surrogate markers into profiler data and/or further comprising training meta-classifiers using the profiler data for distinguishing between individuals with a subsequent transition or non-transition to psychosis.

12. A method of determining a psychosis risk of an individual by determining a pattern or classification and/or in order to determine a psychosis progression or regression, by applying or repeating the method according to claim 1.

13. A method for detecting an adaptive pattern recognition for psychosis risk modeling comprising:
   a. automatically constructing—at least one risk quantification or classification system based upon brain images and data mining;
   b. automatically generating a second risk quantification or classification system based upon genomic and/or metabolomics information and data mining; and
   c. processing the first and second risk quantification or classification systems by data mining computing so as to create a meta-level risk quantification data to automatically quantify psychosis risk at a single subject level and creating and personalizing diagnostic streams by one or more of the following steps:
   a. initializing agents for a given diagnostic, comprising agents for data acquisition, processing and/or result reporting;
   b. forming modality-specific diagnostic layers that have a built-in logic for organising agents into information processing streams, including acquisition, calibration, segmentation, normalization and/or outcome prediction of structural MRI data, monitored by a data quality control agent;
   c. adapting the agent selection process by integrating process variables including prognostic outcome (post-test probability), a multi-axial risk-conferring profile of the help-seeker; and/or diagnostic constraints of given clinical situations.

14. A non-transitory computer related medium carrying out the method according to claim 1.

15. A non-transitory data carrier with a non-transitory computer related medium according to claim 14.

16. A system for an adaptive pattern recognition for psychosis risk modelling, including for carrying out the method of claim 1, comprising at least one of the following features:
   a. a first fully automated risk quantification or classification system based upon the brain images and the data mining;

b. a second risk fully automated risk quantification or classification system based upon the genomic and/or metabolomic information using the data mining;
c. meta-level risk quantification data adapted to further process the first and second risk quantification or classification systems by data mining computing so as to automatically quantify psychosis risk at the single-subject level in new test subjects;
d. a dimensionality reduction of uni-modal data
e. fusion of diverse uni-modal base learners preferable using an ensemble learning method; and
f. further creation and personalisation of diagnostic streams.

17. The system according to claim 16, further comprising—a monitoring psychosis risk component which is adapted to determine the psychosis progression or regression by repeating the automatic quantifying psychosis risk determination or classification.

18. A telemedicine system comprising the features of claim 17 and/or with encrypted data being able to be decrypted by authorized user devices.

* * * * *